(12) United States Patent
Vrana et al.

(10) Patent No.: US 8,527,215 B2
(45) Date of Patent: Sep. 3, 2013

(54) AUTOMATED INSPECTION SYSTEM AND METHOD FOR NONDESTRUCTIVE INSPECTION OF A WORKPIECE USING INDUCTION THERMOGRAPHY

(75) Inventors: Johannes L. Vrana, Berlin (DE); Hubert Mooshofer, Munich (DE); Matthias Goldammer, Munich (DE); Max Rothenfusser, Munich (DE); Wolfgang Heine, Unterhaching (DE)

(73) Assignee: Siemens Energy, Inc., Orlando, FL (US)

( * ) Notice: Subject to any disclaimer, the term of this patent is extended or adjusted under 35 U.S.C. 154(b) by 622 days.

(21) Appl. No.: 12/779,204

(22) Filed: May 13, 2010

(65) Prior Publication Data

US 2010/0292938 A1 Nov. 18, 2010

Related U.S. Application Data

(60) Provisional application No. 61/178,770, filed on May 15, 2009, provisional application No. 61/178,783, filed on May 15, 2009.

(51) Int. Cl.
*G01B 5/28* (2006.01)
*G06F 11/30* (2006.01)

(52) U.S. Cl.
USPC .............. 702/35; 702/182; 702/183; 702/184

(58) Field of Classification Search
USPC .............................. 702/35, 121–123, 179–189
See application file for complete search history.

(56) References Cited

U.S. PATENT DOCUMENTS

| 4,109,508 A * | 8/1978 | Fukuyama ........................ 374/5 |
| 4,173,970 A | 11/1979 | Momin |
| 4,849,885 A | 7/1989 | Stillwagon et al. |
| 4,854,724 A | 8/1989 | Adams et al. |
| 5,124,640 A | 6/1992 | Chern |
| 5,293,119 A | 3/1994 | Podney |
| 5,386,117 A | 1/1995 | Piety |

(Continued)

FOREIGN PATENT DOCUMENTS

| EP | 2141489 A1 | 1/2010 |
| WO | WO 2008/071204 A1 * | 6/2008 |
| WO | WO 2010009918 | 1/2010 |

OTHER PUBLICATIONS

Netzelmann, et al, "Induction Thermography as a Tool for Reliable Detection of Surface Defects in Forged Components" 17th World Conference on Nondestructive Testing, Oct. 25-28, 2008, Shanghai China.

(Continued)

*Primary Examiner* — Phuong Huynh

(57) ABSTRACT

Automated inspection system and method are provided for nondestructive inspection and evaluation of an electrically-conductive workpiece based on induction thermography. A movable carriage (15) may be arranged to translate the workpiece in an inspection location (18). An induction coil 20 is disposed at the inspection location. The induction coil is responsive to an excitation current to induce a flow of electrical current in a region of interest of the workpiece. A thermographic camera (22) is disposed at the inspection location. The thermographic camera is arranged to capture data indicative of a thermal response resulting from the flow of electrical current. A computer system (30) is configured to process the data from the thermographic camera to generate an indication of a presence of a discontinuity (e.g., a subsurface crack) in the workpiece.

20 Claims, 4 Drawing Sheets

(56) References Cited

U.S. PATENT DOCUMENTS

| | | |
|---|---|---|
| 5,562,345 A | 10/1996 | Heyman et al. |
| 5,637,871 A | 6/1997 | Piety |
| 5,675,149 A | 10/1997 | Wood et al. |
| 6,000,844 A | 12/1999 | Cramer |
| 6,516,084 B2 | 2/2003 | Shepard |
| 6,517,236 B2 | 2/2003 | Sun et al. |
| 6,617,847 B2 | 9/2003 | Mitra et al. |
| 6,674,292 B2 | 1/2004 | Bray et al. |
| 6,751,342 B2 | 6/2004 | Shepard |
| 6,856,662 B2 | 2/2005 | Glass et al. |
| 7,485,882 B2 | 2/2009 | Zombo et al. |
| 2002/0050566 A1 | 5/2002 | Nilsson |
| 2002/0079452 A1 | 6/2002 | Roney, Jr. et al. |
| 2005/0008215 A1 | 1/2005 | Shepard |
| 2005/0270037 A1 | 12/2005 | Haynes |
| 2007/0288177 A1 | 12/2007 | Rothenfusser |
| 2008/0067455 A1* | 3/2008 | Zombo et al. ............. 250/504 R |
| 2009/0046758 A1 | 2/2009 | Baumann |

OTHER PUBLICATIONS

Shepard, "Back to Basics", The American Society for Nondestructive Testing, Jul. 2007, pp. 1-19.

Vrana, et al, "Mechanisms and Models for Crack Detection With Induction Thermography", Review of Quantative Nondestructive Evaluation, vol. 27, ed by D.O. Thompson and D.E. Chimenti, p. 475-482.

Starman, "Automated System for Crack Detection Using Infrared Thermographic Testing", 17th World Conference on Nondestructive Testing Oct. 25-28, Shanghai China.

Vrana, et al, "Induction and Conduction Thermography: Optimizing the Electromagnetic Excitation Towards Application", AIP Conf. Proc.—Mar. 3, 2009—vol. 1096, pp. 518-525.

Goldammer, et al. "Automated Induction Thermography of Generator Components", Review of Quantitative Nondestructive Evaluation, AIP Conference Proceedings, vol. 1211, pp. 451-457, Feb. 2010.

* cited by examiner

AUTOMATED INSPECTION SYSTEM AND METHOD FOR NONDESTRUCTIVE INSPECTION OF A WORKPIECE USING INDUCTION THERMOGRAPHY

RELATED APPLICATIONS

This application claims benefit of U.S. provisional patent application No. 61/178,770, and U.S. provisional patent application No. 61/178,783, each filed on May 15, 2009 and respectively incorporated by reference herein in their entirety.

FIELD OF THE INVENTION

The present invention is generally related to nondestructive inspection and evaluation (NDE) of components, and, more particularly, to an automated inspection system and method for NDE of components based on induction thermography.

BACKGROUND OF THE INVENTION

Operation of large rotating machinery can produce substantial mechanical forces that can result in highly-stressed components whose structural integrity needs to be evaluated on periodic basis. For example, electric power generators, as may be used in a power generation plant, include a rotor arranged with a plurality of coils. To lock the coils into position, rotor wedges may be used. The rotor wedges may be constructed from non-magnetic steel and coated with a copper coating, for example. During operation of the generator, rotor components, including the rotor wedges, are subjected to relative large centrifugal forces. In the event of a structural malfunction of any such component, substantial damage could occur to the machinery involved, e.g., the generator and/or a turbine connected to the generator.

Accordingly, such components are inspected to be requalified for further use when the machinery is serviced. For example, it is known to use a fluorescent penetrant to inspect the rotor wedges. This inspection technique has proven to be reliable but suffers from at least the following drawbacks: The coating has to be removed from the components before inspection and the reusable components have to be recoated after the inspection, which leads to substantial costs and delays in view of the relatively large number of components that may be involved. For example, there may be several hundred components per generator. In view of the foregoing considerations, it is desirable to provide an improved inspection system and/or inspection methodology that reliably and in a cost-effective manner avoids or reduces the drawbacks discussed above.

BRIEF DESCRIPTION OF THE DRAWINGS

Aspects of the invention are explained in the following description in view of the drawings where.

DETAILED DESCRIPTION OF THE INVENTION

Figure 1:
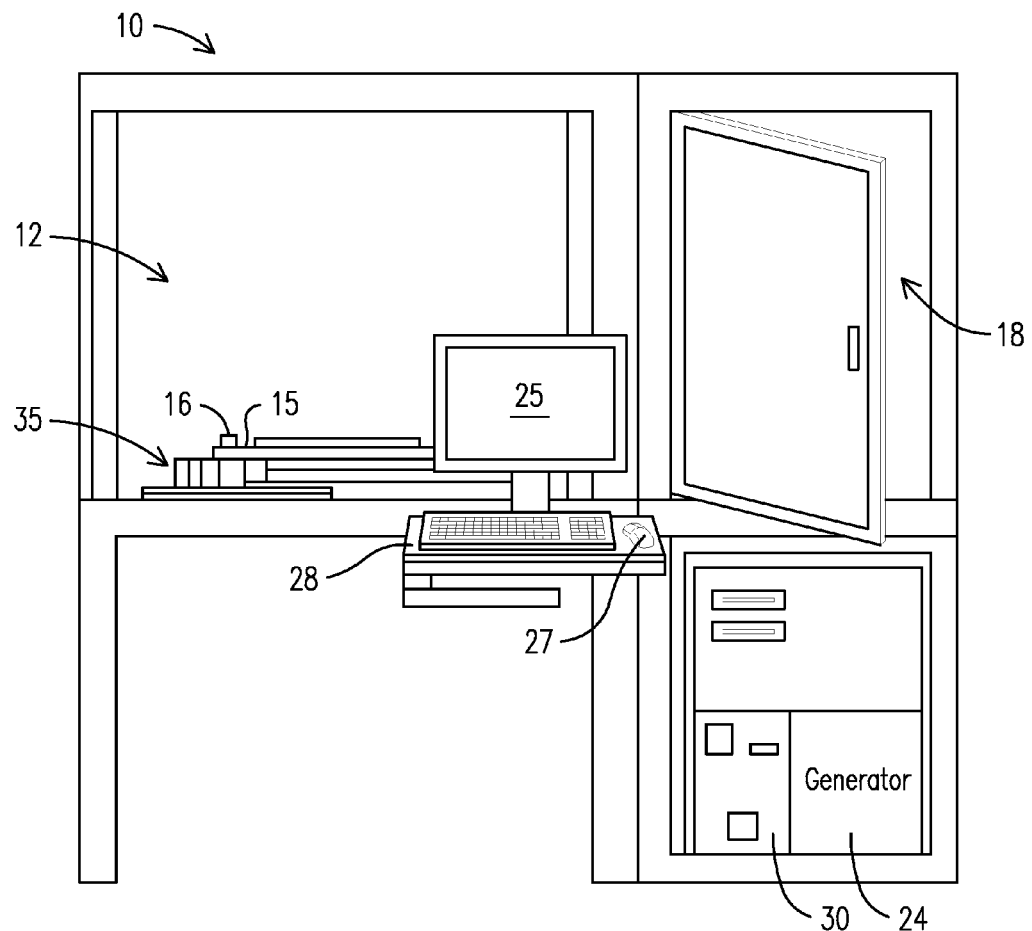
FIG. 1 shows a schematic representation of an automated inspection system embodying aspects of the present invention.

FIG. 1 is a schematic of an automated inspection system 10 embodying aspects of the present invention. Inspection system 10 is arranged for nondestructive inspection and evaluation (NDE) of components based on induction thermography. As will be appreciated by one skilled in the art, in induction thermography an alternating current (e.g., excitation current) in an inductor coil, induces a current in an electrically-conducting material—a workpiece or component to be inspected, such as rotor wedges or other components of rotating machinery, or any component exposed to relatively high mechanical stresses—placed proximate to the inductor coil. If a structural defect (e.g., a crack or other subsurface discontinuity) is present in the workpiece, the current flow is locally disrupted, resulting in an altered current density distribution, and therefore in an altered heating pattern around the area of the defect.

A penetration depth s of the induced current (e.g., skin effect) may be determined from the following equation:

$$s = \frac{1}{\sqrt{\mu_r \mu_0 \sigma \pi f}}$$

In an example case of rotor wedges, since such components are typically made from non-magnetic steel ($\mu_r=1$, $\sigma=1.7$ S/m) for an example frequency of $f=150$ kHz, s would be approximately 1 mm, and for an example frequency of $f=1500$ Hz, s would be approximately 10 mm. Additionally, since a conductive coating on the rotor wedge may be relatively thin (e.g., <0.1 mm), a penetration depth of 1 mm would be sufficient to detect structural defects below the coating. It will be appreciated that standard eddy current-based devices lack the necessary sensitivity to detect sub-surface defects when applied to components with highly conducting coatings, such as rotor wedges.

In one example embodiment, automated inspection system 10 may include a loading bay 12 where one or more workpieces to be inspected may be secured on a movable carriage 15 that can transport (e.g., using straight-line translation motion) at a constant speed or in step-wise motion the one or more workpieces to an inspection location 18.

Figure 2:
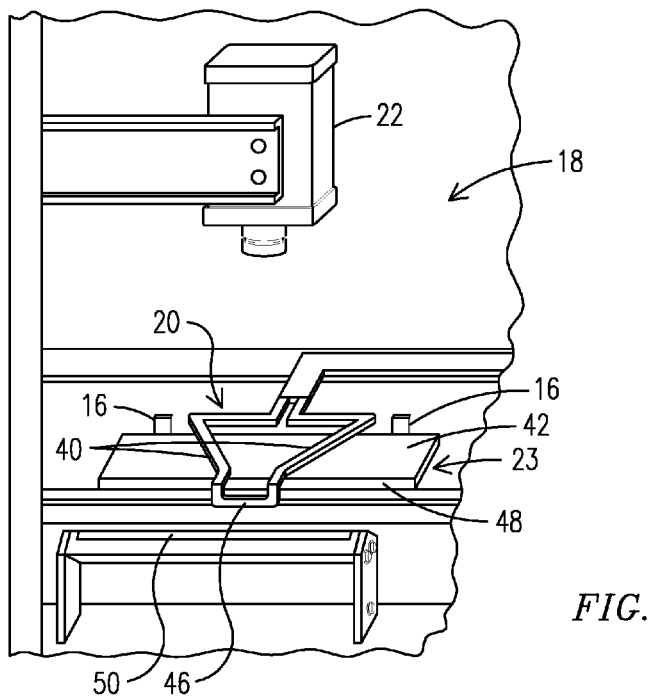
FIGS. 2 and 3 respectively illustrate schematic representations of example embodiments of an induction coil, thermographic camera and reflector as may be arranged in an automated inspection system to simultaneously inspect different portions of an example workpiece, e.g., a workpiece having a cuboidal shape.

As shown in FIG. 2, inspection location 18 accommodates an induction coil 20 and a relatively high-speed thermographic camera 22 (e.g., an infrared camera (IR) camera) to inspect a workpiece 23. In one example embodiment, thermographic camera 22 may operate in the mid-wave range of the infrared spectrum and to appropriately capture the relatively fast heat diffusion of steel, may record approximately in the order of 400 frames per second, as the workpiece passes by a field of view of camera 22. In one example embodiment, camera 22 may use a focal plane array sensor (e.g., an array of photodiodes) to measure the emitted radiance from the component being inspected.

In inspection location 18, the component being inspected is inductively excited, either continuously or intermittently, in response to current supplied to induction coil 20 from an induction generator 24 (FIG. 1). Induction generator 24 is configured to deliver a sufficient electrical power level (e.g., up to approximately 10 kW or more) into the coil to appropriately excite the workpiece being inspected. In one example embodiment, generator 24, connecting cable (not shown) and coil 20 may be cooled by a fluid (e.g., water) circulating in suitable cooling ducts. This may allow uninterrupted operation of such equipment over relatively long periods of time without operation stoppage for equipment cooling.

Data indicative of a resulting heat distribution on the component is recorded with thermographic camera 22, which may be appropriately shielded from infrared radiation from the surroundings. Similarly, inspection location 18 may be enclosed by walls, as may be arranged to protect an operator of the system from electrical currents and/or moving components. The operator may monitor and command operation of inspection system 10 via a display 25, a keyboard 28 or any other suitable input/output interface (e.g., mouse 27) connected to a computer system 30.

Computer system 30 may include appropriate hardware and software configured to process data acquired by thermographic camera 22 to generate an indication of a presence of a discontinuity (e.g., a crack) in the workpiece. That is, computer system 30 is configured to identify heat distribution disturbances likely due to a subsurface structural defect present in the component, such as a crack.

Figure 9:
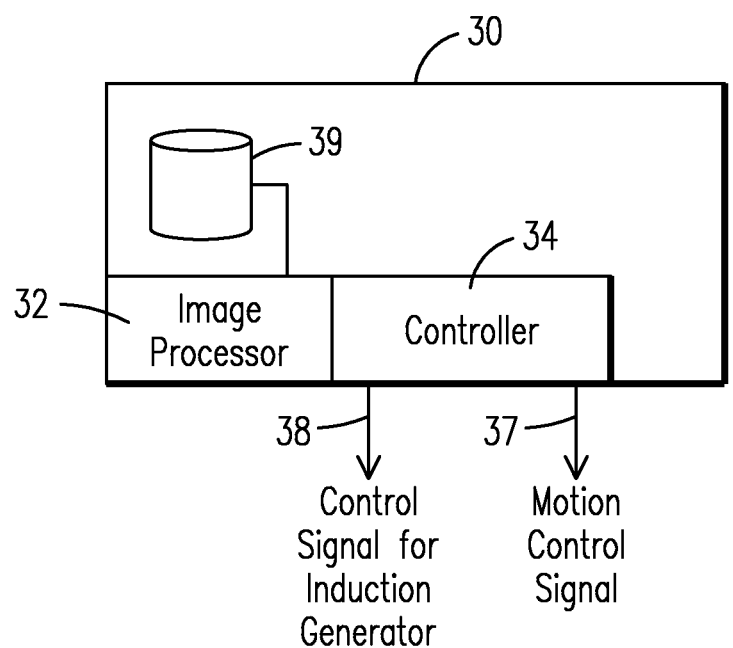
FIG. 9 shows a block diagram of an example computer system as may be used in an automated inspection system embodying aspects of the present invention.

As shown in FIG. 9, computer system 30 in one example embodiment may include an imaging processor 32 to process the data from thermographic camera 22 to generate an image indicative of the discontinuity in the workpiece. Computer system 30 may further include a controller 34 configured to control a translation motion of movable carriage 15. For example, a motion control signal 37 may be supplied to a motorized drive 35 (FIG. 1) coupled to movable carriage 15. Controller 34 may be further configured to coordinate a timing (e.g., with a precision in the order of milliseconds) for controlling (e.g., in response to a control signal 38) the excitation current in the induction coil with respect to an activation of the thermographic camera to capture the data indicative of the thermal response. Computer system 30 may further include a storage and retrieval unit 39 configured to store and retrieve digital IR images useful for determining the structural assessment of the component being inspected. The data is appropriately processed so that the resulting images have sufficient contrast and resolution to visibly indicate a likely presence of a defect in the component.

It will be appreciated that the foregoing components of computer system 30 may take the form of a hardware embodiment, a software embodiment or an embodiment containing both hardware and software components, which may include firmware, resident software, microcode, etc. Furthermore, aspects of such components may take the form of a computer program product accessible from a computer-usable or computer-readable medium providing program code for use by or in connection with a computer or any instruction execution system. Examples of a computer-readable medium include a semiconductor or solid-state memory, magnetic tape, a removable computer diskette, a random access memory (RAM), a read-only memory (ROM), a rigid magnetic disk and an optical disk. Current examples of optical disks include compact disk—read only memory (CD-ROM), compact disk—read/write (CD-RNV) and DVD.

A processing device suitable for storing and/or executing program code may include at least one processor coupled directly or indirectly to memory elements through a system bus. The memory elements may include local memory employed during actual execution of the program code, bulk storage, and cache memories which provide temporary storage of at least some program code in order to reduce the number of times code must be retrieved from bulk storage during execution. Input/output or I/O devices (including but not limited to keyboards, displays, pointing devices, etc.) can be coupled to the system either directly or through intervening I/O controllers.

Figure 3:
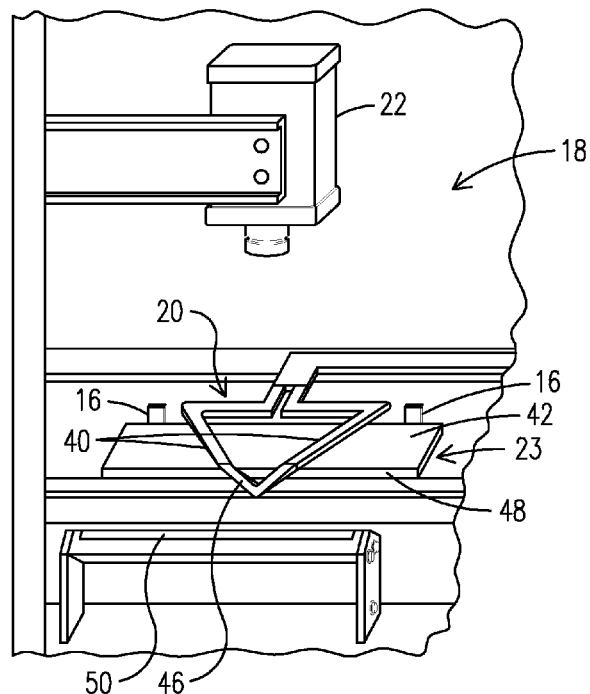

As can be appreciated in FIGS. 2 and 3, in one example embodiment, as may be used for inspecting a workpiece having a cuboidal shape (e.g., rectangular parallelepiped), induction coil 20 may include a first induction coil section 40 arranged to induce a flow of electrical current in a first portion of workpiece 23 (e.g., a top surface 42 of the workpiece). Induction coil 20 may further include a second induction coil section 46 positioned at an angle relative to first induction coil section 40 and coupled (e.g., electromechanically coupled) to first induction coil section 40. Second induction coil section 46 may be arranged to induce a flow of electrical current in a second portion of the workpiece (e.g., a lateral surface 48 of workpiece 23).

As can be further appreciated in FIGS. 2 and 3, a reflector 50 (e.g., a plane reflector) may be arranged to reflect within a field of view of thermographic camera 22, data indicative of a thermal response from at least one of the first and second portions of the workpiece. For example, reflector 50 may be positioned to reflect into the field of view of thermographic camera 22 radiance from lateral surface 48. It will be appreciated that reflector 50 may be made up of one or more reflecting surfaces. It will be further appreciated that reflector 50 need not be a stationary component since it may be connected to an appropriate position-adjusting mechanism (e.g., pivoting mechanism) to adjust the orientation of the reflector to, for example, enhance the size of the surface area being inspected by thermographic camera 22.

It will be appreciated that the foregoing example embodiment may be attractive because in a single inspection action, one can simultaneously inspect at least two different regions (e.g., regions of the workpiece angled relative to one another) without having to reposition the workpiece. It will be appreciated that in a general case, the first and second induction coil sections 40 and 46 need not be limited to coil sections positioned at an angle with respect to one another. It is contemplated that such sections could be adapted to address other needs that may arise in a given application. For example, one of the coil sections may be configured differently (e.g., different size) than the other section to more appropriately couple inductive energy into a region of a workpiece that may be made of a different material (e.g., having different electromagnetic properties) than the remainder of the piece.

Figure 4:
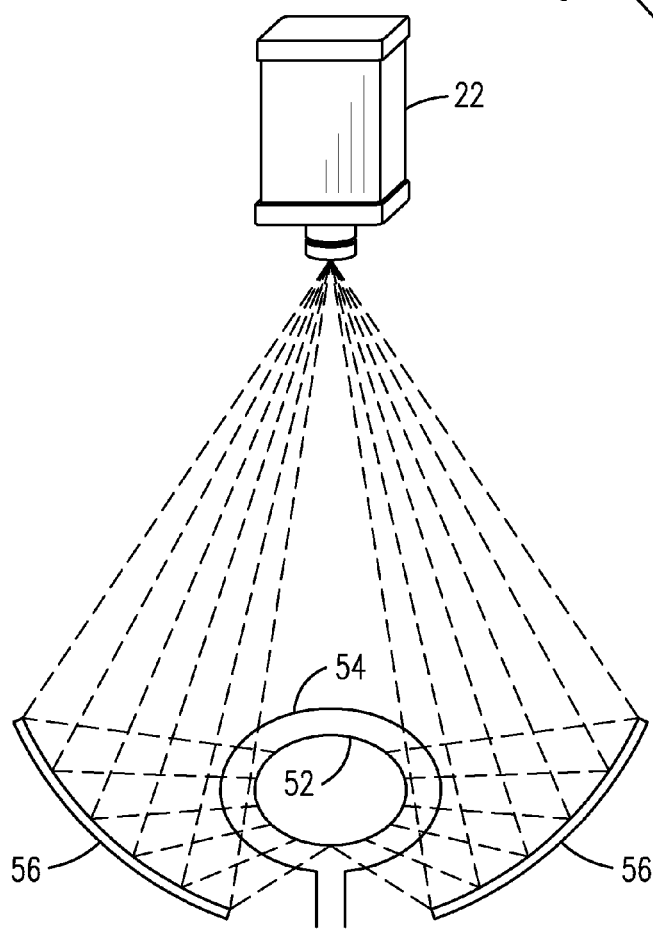
FIG. 4 illustrates a schematic representation of an example embodiment of an induction coil, thermographic camera and reflector as may be arranged in an automated inspection system to inspect another example workpiece, e.g., a workpiece having a generally cylindrical shape.

It will be appreciated that aspects of the present invention are not limited to any specific shape of the workpiece. For example, FIG. 4 illustrates an example embodiment as may be used for inspecting a workpiece 52 having a generally cylindrical shape. In this example, an appropriately curved induction coil 54 may be arranged to induce a flow of electrical current in workpiece 52. A curved reflector 56 (e.g., ellipsoidal shape or any suitable non-planar configuration) may be arranged to reflect within a field of view of thermographic camera 22, data indicative of a thermal response around all or most of the surface area of workpiece 52. This would allow reducing the number of times that one would have to reposition the cylindrical workpiece to fully inspect the workpiece.

Figure 5:
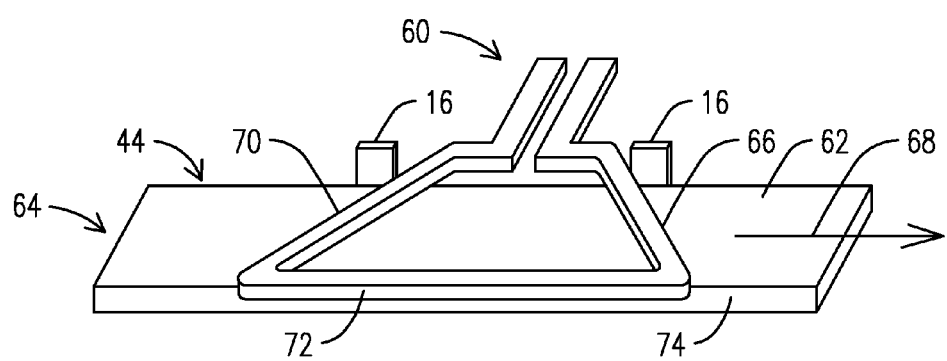
FIGS. 5-7 illustrate respective views of further examples of induction coil configurations as may be used in an automated inspection system embodying aspects of the present invention.

It will be appreciated that an inspection system embodying aspects of the present invention need not include first and second induction coil sections together with a reflector for simultaneously inspecting different regions of the workpiece, as described in the context of FIGS. 2-4. For example, FIG. 5 illustrates an inspection coil 60 that allows inspecting a singular portion (e.g., a top surface 62) of a workpiece 64 per inspection action.

In one example embodiment, induction coil 60 includes a first segment 66 positioned at an angle (e.g., approximately) 45° relative to a longitudinal axis 68 of workpiece 64. Inspection coil 60 further includes a second segment 70 positioned at another angle (e.g., approximately)−45° relative to longitudinal axis 68 of workpiece 64. A third coil segment 72 may be used to electromechanically couple to one another first and second coil segments 66 and 70 of induction coil 60. The example angular alignment of first and second segments 66 and 70 with respect to one another (e.g., jointly spanning an angular range of approximately)90° ensures crack detection regardless of a main direction of propagation of the crack. For example, a crack will offer the largest electrical resistance (e.g., largest thermal response) if the crack is oriented perpendicular relative to the current flow. Conversely, a crack will offer the lowest electrical resistance (e.g., lowest thermal response) if the crack is oriented parallel relative to the current flow. Thus, the foregoing angular positioning of first and second coil segments 66 and 70 ensures appropriate orthogonal components of current flow to detect a crack regardless of a main direction of propagation of the crack. It will be appreciated that for inspection of additional surfaces (e.g., lateral surface 74), workpiece 64 would be repositioned to face the thermographic camera during a separate inspection action.

Figure 6:
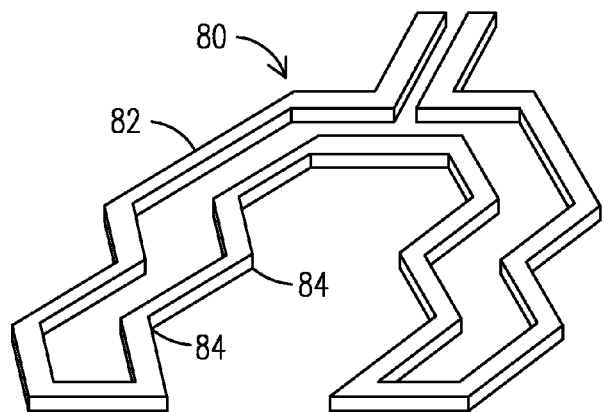
Figure 7:
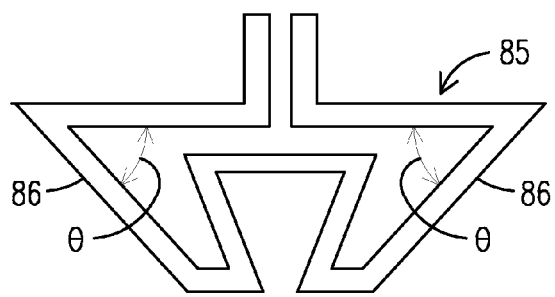

FIGS. 6-7 respectively illustrate an isometric view and a top view of further examples of induction coil configurations as may be used in an automated inspection system embodying aspects of the present invention. For example, FIG. 6 shows an induction coil 80 including a plurality of coil segments 82 arranged to define a plurality of sharp angles 84 (e.g., corners). The zig-zagging arrangement of coil 80 may be useful for scanning a workpiece having a relatively wide width dimension.

FIG. 7 shows an induction coil 85 having coil segments 86 arranged with a mutual angular arrangement (e.g., jointly spanning an angular range of approximately)90°, which as discussed above ensures crack detection regardless of a main direction of propagation of the crack.

Figure 8:
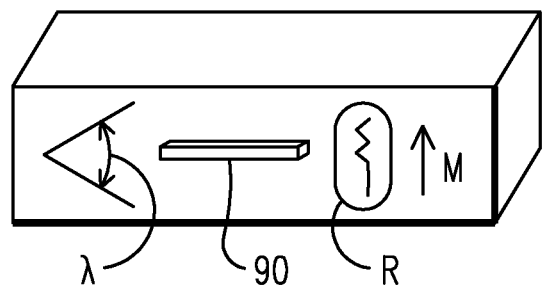
FIG. 8 illustrates an example inspection application where one may probabilistically estimate an expected main direction of crack formation, and further illustrates an example positioning of an inspection coil segment embodying aspects of the present invention.

As illustrated in FIG. 8, there may be certain inspection applications where (prior to the inspection) one may probabilistically, experimentally or otherwise estimate an expected main direction M of crack formation R, and in such applications, an example coil segment 90 may be transversely positioned within an angular range A relative to the expected direction of crack formation. For example, for an expected main direction M of crack formation as shown in FIG. 8, one should not position coil segment 90 in a generally vertical direction. That is, coil segment 90 should not be positioned generally parallel to direction M.

It will be appreciated by those skilled in the art that to ensure relatively constant sensitivity of the inspection, a fixed distance between the component being inspected and the induction coil may be desirable. Since the specific geometrical configuration (e.g., length, width and/or thickness) of a given workpiece may differ depending on the specific application, movable carriage 15 may be provided with an adjustable affixing mechanism (e.g., adjustable positioning tabs 16 or similar position-adjusting structures) at appropriate locations of movable carriage 15. This adjusting mechanism may advantageously eliminate not only adjustments in connection with a spacing distance between the induction coil and the workpiece but also in connection with a focusing adjustment of the thermographic camera.

While various embodiments of the present invention have been shown and described herein, it will be apparent that such embodiments are provided by way of example only. Numerous variations, changes and substitutions may be made without departing from the invention herein. Accordingly, it is intended that the invention be limited only by the spirit and scope of the appended claims.

The invention claimed is:

1. An automated inspection system for nondestructive inspection and evaluation of an electrically-conductive workpiece based on induction thermography, the system comprising:
   a movable carriage arranged to translate the workpiece in an inspection location;
   an induction coil disposed at the inspection location, the induction coil responsive to an excitation current to induce a flow of electrical current in a region of interest of the workpiece;
   a thermographic camera disposed at the inspection location, the thermographic camera arranged to capture data indicative of a thermal response resulting from the flow of electrical current;
   a reflector arranged to reflect within a field of view of the thermographic camera, data indicative of a thermal response from a portion of the workpiece that otherwise would not be captured by the thermographic camera; and
   a computer system configured to process the data from the thermographic camera to generate an indication of a presence of a discontinuity in the workpiece.

2. The automated inspection system of claim 1, wherein the induction coil comprises a first induction coil section arranged to induce a flow of electrical current in a first portion of the workpiece, wherein the induction coil further comprises a second induction coil section coupled to said first induction coil section, the second induction coil section arranged to induce a flow of electrical current in a second portion of the workpiece, wherein the first and the second portions of the workpiece comprise different portions of the workpiece.

3. The automated inspection system of claim 2, wherein the first and second induction coil sections are positioned at an angle with respect to one another to inductively excite first and second portions of the workpiece angled relative to one another.

4. The automated inspection system of claim 2, wherein the first induction coil section comprises at least two coil segments, wherein said at least two coil segments of the first induction coil section have a mutual angular arrangement chosen to detect the discontinuity regardless of a main direction of propagation of the discontinuity relative to said at least two coil segments of the first induction coil section.

5. The automated inspection system of claim 2, wherein the second induction coil section comprises at least two coil segments, wherein said at least two coil segments of the second induction coil section have a mutual angular arrangement chosen to detect the discontinuity regardless of a main direction of propagation of the discontinuity relative to said at least two coil segments of the second induction coil section.

6. The automated inspection system of claim 1, wherein the reflector is a plane mirror.

7. The automated inspection system of claim 1, wherein the reflector is a curved mirror.

8. The automated inspection system of claim 1, wherein the discontinuity comprises a crack and wherein said induction coil comprises at least a coil segment transversely positioned within an angular range relative to an expected direction of propagation of the crack.

9. The automated inspection system of claim 1, wherein the computer system comprises an imaging processor to generate an image indicative of the discontinuity in the workpiece.

10. The automated inspection system of claim 1, wherein the computer system comprises a controller configured to control a translation motion of the movable carriage, and further configured to coordinate control of the excitation current in the induction coil with respect to a sequential activation of the thermographic camera to capture the data indicative of the thermal response, as a surface of the workpiece in correspondence with the region of interest passes within a field of view of the camera.

11. An automated inspection system for nondestructive inspection and evaluation of an electrically-conductive workpiece based on induction thermography, the system comprising:
 a movable carriage configured to translate the workpiece in an inspection location;
 an induction coil disposed at the inspection location, wherein the induction coil comprises a first induction coil section arranged to induce a respective flow of electrical current in a first portion of the workpiece, wherein the induction coil further comprises a second induction coil section coupled to said first induction coil section, the second induction coil section arranged to induce a respective flow of electrical current in a second portion of the workpiece, wherein the first and second induction coil sections are positioned at an angle with respect to one another to inductively excite first and second portions of the workpiece angled relative to one another;
 a thermographic camera disposed at the inspection location, the thermographic camera arranged to capture data indicative of a thermal response resulting from the respective flows of electrical current in the first and second portions of the workpiece;
 a reflector arranged to reflect within a field of view of the thermographic camera at least some of the data indicative of the thermal response that otherwise would not be captured by the thermographic camera; and
 a computer system configured to process the data captured by the thermographic camera to generate an indication of a presence of a discontinuity in the workpiece, wherein the computer system comprises a controller configured to control a translation motion of the movable carriage, and further configured to coordinate control of the excitation current in the induction coil with respect to a sequential activation of the thermographic camera to capture the data indicative of the thermal response, as said at least one of the first and second portions of the workpiece, or a reflection of said at least one of the first and second portions passes within the field of view of the camera.

12. The automated inspection system of claim 11, wherein the first induction coil section comprises at least two coil segments, wherein said at least two coil segments of the first induction coil section have a mutual angular arrangement configured to detect the discontinuity regardless of a main direction of propagation of the discontinuity relative to said at least two coil segments of the first induction coil section.

13. The automated inspection system of claim 11, wherein the second induction coil section comprises at least two coil segments, wherein said at least two coil segments of the second induction coil section have a mutual angular arrangement configured to detect the discontinuity regardless of a main direction of propagation of the discontinuity relative to said at least two coil segments of the second induction coil section.

14. A method for nondestructive inspection and evaluation of an electrically-conductive workpiece based on induction thermography, the method comprising:
 controlling motion of a movable carriage so that the workpiece is translated in an inspection location;
 exciting an induction coil disposed at the inspection location to induce a flow of electrical current in a region of interest of the workpiece;
 acquiring with a thermographic camera data indicative of a thermal response resulting from the flow of electrical current;
 arranging a reflector to reflect within a field of view of the thermographic camera, data indicative of a thermal response from a portion of the workpiece that otherwise would not be captured by the thermographic camera; and
 processing the data from the thermographic camera to generate an indication of a presence of a discontinuity in the workpiece.

15. The method of claim 14, arranging in the induction coil a first induction coil section to induce a flow of electrical current in a first portion of the workpiece, coupling a second induction coil section to the first induction coil section to induce a flow of electrical current in a second portion of the workpiece, wherein the first and the second portions of the workpiece comprise different portions of the workpiece.

16. The method of claim 15, arranging the first and second induction coil sections to be positioned at an angle with respect to one another to excite first and second portions of the workpiece angled with respect to one another.

17. The method of claim 15, providing in the first induction coil section at least two coil segments, arranging said at least two coil segments of the first induction coil section to have a mutual angular arrangement configured to detect the discontinuity regardless of a main direction of propagation of the discontinuity relative to said at least two coil segments of the first induction coil section.

18. The method of claim 15, providing in the second induction coil section at least two coil segments, arranging said at least two coil segments of the second induction coil section to have a mutual angular arrangement configured to detect the discontinuity regardless of a main direction of propagation of the discontinuity relative to said at least two coil segments of the second induction coil section.

19. The method of claim 14, wherein the discontinuity comprises a crack and transversely positioning at least a coil segment of the induction coil within an angular range with respect to an expected direction of propagation of the crack.

20. The method of claim 14, further comprising inducing the flow of electrical current beneath an electrically conductive coating of the workpiece.

* * * * *